(12) United States Patent
Majumdar et al.

(10) Patent No.: US 11,298,312 B2
(45) Date of Patent: *Apr. 12, 2022

(54) COMPOSITION COMPRISING NIACINAMIDE AND PICOLINAMIDE

(71) Applicant: Conopco, Inc., Englewood Cliffs, NJ (US)

(72) Inventors: Amitabha Majumdar, Bangalore (IN); Mruthyunjaya Swamy Mathapathi, Bangalore (IN)

(73) Assignee: CONOPCO, INC., Englewood Cliffs, NJ (US)

( * ) Notice: Subject to any disclaimer, the term of this patent is extended or adjusted under 35 U.S.C. 154(b) by 93 days.

This patent is subject to a terminal disclaimer.

(21) Appl. No.: 16/822,183

(22) Filed: Mar. 18, 2020

(65) Prior Publication Data

US 2020/0230045 A1 Jul. 23, 2020

Related U.S. Application Data

(63) Continuation of application No. 15/765,015, filed as application No. PCT/EP2016/073626 on Oct. 4, 2016, now Pat. No. 10,660,840.

(30) Foreign Application Priority Data

Oct. 5, 2015 (EP) ..................................... 15188360

(51) Int. Cl.
| | | |
|---|---|---|
| A61K 8/67 | (2006.01) | |
| A61K 8/49 | (2006.01) | |
| A61Q 15/00 | (2006.01) | |
| A61Q 17/00 | (2006.01) | |
| A61Q 19/02 | (2006.01) | |
| A61Q 19/10 | (2006.01) | |

(52) U.S. Cl.
CPC ............ *A61K 8/675* (2013.01); *A61K 8/4926* (2013.01); *A61Q 15/00* (2013.01); *A61Q 17/005* (2013.01); *A61Q 19/02* (2013.01); *A61Q 19/10* (2013.01); *A61K 2800/70* (2013.01)

(58) Field of Classification Search
None
See application file for complete search history.

(56) References Cited

U.S. PATENT DOCUMENTS

| | | | |
|---|---|---|---|
| 5,411,741 A | 2/1995 | Zaias | |
| 5,582,817 A | 10/1996 | Otsu | |
| 8,084,049 B2 | 12/2011 | Weidner | |
| 9,227,090 B2 | 5/2016 | Madison | |
| 10,660,840 B2 * | 5/2020 | Majumdar | .............. A61Q 15/00 |
| 10,952,952 B2 * | 3/2021 | Damodaran | ........... A61Q 19/10 |
| 2003/0105034 A1 | 6/2003 | Weidner | |
| 2003/0203943 A1 | 10/2003 | Weidner | |
| 2009/0105188 A1 | 4/2009 | Giannone et al. | |
| 2010/0184768 A1 * | 7/2010 | Stock | ........................ A61P 1/04 514/237.5 |
| 2014/0161750 A1 * | 6/2014 | Balshi | ...................... A61K 8/27 424/60 |
| 2018/0280278 A1 | 10/2018 | Damodaran | |

FOREIGN PATENT DOCUMENTS

| | | |
|---|---|---|
| CN | 103976889 | 8/2014 |
| CN | 105682748 | 6/2016 |
| EA | 008023 | 2/2007 |
| EP | 1283033 | 2/2003 |
| EP | 2522331 | 11/2012 |
| EP | 2742942 | 6/2014 |
| JP | 2003267817 | 9/2003 |
| JP | 2004123554 | 4/2004 |
| JP | 2005537238 | 12/2005 |
| WO | WO9947141 | 9/1999 |
| WO | WO2004000333 | 12/2003 |
| WO | WO2010002586 | 1/2010 |
| WO | WO2011133692 | 10/2011 |
| WO | WO2013030794 | 3/2013 |
| WO | WO2015061512 | 4/2015 |
| WO | WO2015172801 | 11/2015 |

OTHER PUBLICATIONS

Pierre Kyme et al.; C/EBP epsilon mediates nicotinamide-enchanced clearance of *Staphylococcus aureus* in mice; Journal of Clinical Investigation; Sep. 4, 2012; pp. 3316-3329; vol. 122, No. 9; United States of America.

Pourahmadi Mohammad et al.; Evaluation of the Effect of Topical Picolinamide on Epidermal Melasma; Biosciences Biotechnology Research Asia; 2014; pp. 1047-1050; XP2757361; vol. 11 No 2.

Nikitakis et al.; Picolinamide; International Cosmetic Ingredient Dictionary and Handbook; 2014; p. 2623; XP002767164; 15th Edition, vol. 2.

Hakozaki et al.; The effect of niacinamide on reducing cutaneous pigmentation and suprression of melanosome transfer; British Journal of Dermatology; 2002; pp. 20-31; XP002333293; vol. 147, No. 1.

IPRP2 in PCTEP2016073617; Oct. 5, 2017.

Written Opinion 2 in PCTEP2016073626; dated Sep. 19, 2017.

Search Report and Written Opinion in PCTEP2016073626; dated Feb. 28, 2017.

Hongli Sun et al,; Field-amplified sample injection for the determination; Analytical Methods; 2013; pp. 5615-5621; 5.

(Continued)

*Primary Examiner* — Aradhana Sasan

(74) *Attorney, Agent, or Firm* — Krista A. Kostiew

(57) ABSTRACT

The present invention relates to a topical composition and more particularly a topical composition for antimicrobial benefit. According to the present invention there is provided a topical composition comprising Niacinamide and picolinamide wherein the molar ratio of Niacinamide to picolinamide is from 1:20 to 20:1.

18 Claims, No Drawings

(56) References Cited

OTHER PUBLICATIONS

Search Report & Written Opinion in PCTEP2016073617; dated Feb. 13, 2017.
Search Report & Written Opinion in EP15188360; dated May 17, 2016.
IPRP2 in PCTEP2016073626; Jan. 2, 2018.
Co-Pending U.S. Appl. No. 15/764,968.
M.H. Braff and R.L. Gallo; Antimicrobial Peptides; An Essential Component of the Skin Defensive Barrier; 2006; pp. 1-20; vol. 306:91-100; Springer-Verlag Berlin Heidelberg.

* cited by examiner

COMPOSITION COMPRISING NIACINAMIDE AND PICOLINAMIDE

CROSS-REFERENCE TO RELATED APPLICATIONS

This application is a continuation of U.S. patent application Ser. No. 15/765,015. This application claims priority to U.S. patent application Ser. No. 15/765,015, filed on Mar. 30, 2018, and International Patent Application No. PCT/EP2016/073626, filed on Oct. 4, 2016 and European Patent Application No. 15188360.0, filed on Oct. 5, 2015, all of which are incorporated herein by reference in their entireties.

TECHNICAL FIELD

The present invention relates to a topical composition and more particularly a topical composition for antimicrobial benefit.

BACKGROUND OF THE INVENTION

People try to take good care of the external surface of their bodies. Specific skin related issues that people care about include good skin health free of infections, good skin tone and skin hygiene. Skin hygiene is generally achieved by keeping them free of infections. One way to tackle infections is to treat them with antimicrobials after the infection has set in. Another approach is to leave a minimal amount of antimicrobial active on the surface so that any invading microorganism is killed or inactivated to minimize spread of diseases. Yet another approach is improving the innate immunity of the desired surface. Some of the bacteria like *E. coli*, *S. aureus* are generally exists on the skin. These bacteria does not have any pathogenic effect per se on the skin. However when this goes inside the body through ingestion, they induces their pathogenic effect. Therefore keeping the external surface of the body e.g. hand, scalp free of this bacteria helps in achieving the desired hygiene.

AMPs form an integral part of the skin's own defense system. AMPs were initially discovered in insects and in animals and ever since their initial discovery AMPs are regarded as promising antimicrobials. AMPs are ubiquitous in nature and they typically exhibit a broad spectrum of activity against invading bacteria, fungi, enveloped viruses and parasites (Braff and Gallo, 2006. AMPs are generally short peptides and in humans about 90 different AMPs are reported to be present. AMPs in general have two major physical features and they are—a) cationic charge and b) a significant proportion of hydrophobic residues. The cationic charge of the AMPs promotes selectivity for negatively charged microbial cytoplasmic membranes whereas the hydrophobicity facilitates interactions with the cell membrane of the microbial species.

Niacinamide is known in the art for inducing AMP generation on the skin thereby providing antimicrobial benefit.

WO 2015/172801 (Unilever, 2015) discloses a new use of niacinamide for triggering generation of AMPs (antimicrobial peptides) on skin. This has application in improving the immunity of skin, scalp and oral cavity against attack by microorganisms.

The present inventors have been working to provide hygiene benefits to consumers through the route of enhancing the AMP levels in the skin.

It is therefore an object of the present invention to provide an antimicrobial composition.

It is another object of the present invention to provide an antimicrobial composition for through the route of enhancing the AMP levels in the skin.

It is yet another object of the present invention to provide an antimicrobial composition for leave-on application, which has antimicrobial efficacy for long time.

The present inventors while working extensively on this have surprisingly found that a composition comprising Niacinamide and picolinamide in a particular ratio provides significantly better antimicrobial benefit by inducing AMP when compared to Niacinamide alone, thereby satisfies one or more of the above said objects.

SUMMARY OF THE INVENTION

In a first aspect, the present invention provides a topical composition comprising Niacinamide and picolinamide wherein the molar ratio of Niacinamide to picolinamide is from 1:20 to 20:1.

In a second aspect, the present invention provides a method of cleaning or disinfecting a surface comprising the steps of applying a composition of the first aspect on to said surface.

In a third aspect the present invention provides a use of a composition comprising Niacinamide and picolinamide for improved antimicrobial benefit.

In a fourth aspect the present invention provides a use of a composition comprising Niacinamide and picolinamide for inducing secretion of anti-microbial peptides (AMPs) when applied on an external surface of the human body.

Any feature of one aspect of the present invention may be utilized in any other aspect of the invention. The word "comprising" is intended to mean "including" but not necessarily "consisting of" or "composed of." In other words, the listed steps or options need not be exhaustive. Except in the operating and comparative examples, or where otherwise explicitly indicated, all numbers in this description indicating amounts of material or conditions of reaction, physical properties of materials and/or use are to be understood as modified by the word "about". Numerical ranges expressed in the format "from x to y" are understood to include x and y. When for a specific feature multiple preferred ranges are described in the format "from x to y", it is understood that all ranges combining the different endpoints are also contemplated.

DETAILED DESCRIPTION OF THE INVENTION

The present invention provides a topical composition comprising Niacinamide and picolinamide wherein the molar ratio of Niacinamide to picolinamide is from 1:20 to 20:1.

One of the component of the composition of the present invention is Niacinamide. Niacinamide is also known as nicotinamide and as pyridine-3-carboxamide is the active, water soluble form of vitamin B3. It is essential to the coenzymes NADH and NADPH and therefore for over 200 enzymatic reactions in the body including ATP formation.

Another essential component of the composition of the present invention is picolinamide. Nicotinamide, a pyridine 3-carboxamide has 2 other positional isomers by substitution at 2, and 4 position of the pyridine ring, picolinamide (pyridine 2-carboxamide) and isonicotinamide (pyridine 4-carboxamide) respectively.

The molar ratio of niacinamide to picolinamide is from 1:20 to 20:1, preferably from 1:15 to 15:1, more preferably from 1:10 to 10:1, further more preferably from 1:8 to 8:1, even more preferably 1:5 to 5:1 and most preferably from 1:2 to 2:1. The present inventors have found that, niacinamide and picolinamide at this particular ratios provide synergistic antimicrobial benefit in terms of AMP generation. Therefore, the composition preferably comprises a synergistic combination of niacinamide and picolinamide.

There is no upper limit of the amount of niacinamide in the composition. However, preferably niacinamide is present in the composition in an amount from 0.1 to 20%, more preferably from 1 to 10%, further more preferably from 1 to 5% and most preferably from 1 to 3% by weight of the composition.

Additionally, there is also no upper limit of the amount of picolinamide in the composition. However, preferably picolinamide is present in the composition in an amount from 0.1 to 20%, more preferably from 1 to 10%, further more preferably from 1 to 5% and most preferably from 1 to 3% by weight of the composition.

The composition of the present invention preferably comprises a cosmetically acceptable base.

The cosmetically acceptable base is preferably a cream, lotion, gel or emulsion.

Personal care compositions (leave-on) may be prepared using different cosmetically acceptable emulsifying or non-emulsifying systems and vehicles. A highly suitable base is a cream. Vanishing creams are especially preferred. Vanishing cream bases generally comprise 5 to 25% fatty acid and 0.1 to 10% soap. Vanishing cream base gives a highly appreciated matty feel to the skin. C12 to C20 fatty acids are especially preferred in vanishing cream bases, further more preferred being C14 to C18 fatty acids. The most preferred fatty acid is stearic acid. The fatty acid in the composition is more preferably present in an amount in the range of 5 to 20% by weight of the composition. Soaps in the vanishing cream base include alkali metal salt of fatty acids, like sodium or potassium salts, most preferred being potassium stearate. The soap in the vanishing cream base is generally present in an amount in the range of 0.1 to 10%, more preferably 0.1 to 3% by weight of the composition. Generally, the vanishing cream base in personal care compositions is prepared by taking a desired amount of total fatty matter and mixing with potassium hydroxide in desired amounts. The soap is usually formed insitu during the mixing.

An especially suitable cosmetically acceptable base is one which comprises a water-in-oil emulsion comprising silicone oils as the continuous phase. The water in oil emulsions preferably comprise a cross-linked silicone elastomer blend.

Inclusion of silicone elastomer blend in a water-in-oil emulsion may be used as the cosmetically acceptable base for preparing the compositions of the present invention. While silicone fluids may be used, silicone elastomers which are cross-linked, are especially preferred. In contrast to silicone fluid polymers, the physical properties of elastomers are typically dependent on the number of cross-linkages, rather than molecular weight. The ability of silicone elastomers to swell makes them ideal thickeners for oil phases. The elastomers have a very smooth and soft feel when applied to skin or hair. They can also be used as delivery agents for fragrances, vitamins and other additives in cosmetic compositions.

Suitable silicone elastomer blends or gels which are commercially available and suitable for inclusion in the composition of the invention and found to provide the enhanced stability are: Dow Corning® EL-8051 IN Silicone Organic Elastomer Blend [INCI Name: Isodecyl Neopentanoate (and) Dimethicone/Bis Isobutyl PPG-20 Crosspolymer]; EL-8050 [INCI Name: Isododecane (and) Dimethicone/Bis-Isobutyl PPG 20 Crosspolymer] DC 9040, DC9041, DC9045 (Dimethicone crosspolymer); DC 9506, 9509 (Dimethicone vinyl dimethicone crosspolymer); Shin-Etsu KSG-15, KSG-16, KSG-17 (Dimethicone vinyl dimethicone crosspolymer). It is further preferred that the composition comprises 5 to 50% silicone elastomer by weight of the composition.

The composition of the present invention may optionally comprises of skin lightening agents e.g. aloe extract, ammonium lactate, arbutin, azelaic acid, kojic acid, butyl hydroxy anisole, butyl hydroxy toluene, citrate esters, 3 diphenyl propane derivatives, 2, 5 dihydroxybenzoic acid and its derivatives, ellagic acid, fennel extract, gluco pyranosyl-1-ascorbate, gluconic acid, glycolic acid, green tea extract, hydroquinone, 4 hydroxyanisole and its derivatives, 4-hydroxy benzoic acid derivatives, hydroxycaprylic acid, lemon extract, linoleic acid, magnesium ascorbyl phosphate, mulberry root extract, 2,4 resorcinol derivatives, 3,5 resorcinol derivatives, salicylic acid, vitamins like vitamin B6, vitamin B12, vitamin C, vitamin A, a dicarboxylic acid, resorcinol derivatives, hydroxycarboxylic acid like lactic acid and their salts e.g. sodium lactate, and mixtures thereof.

Additionally, though not preferred, the composition may have sunscreen. Any sunscreen that can be suitably used with the base may be added. Both, UVA and UVB sunscreens may preferably be added.

The composition of the invention may preferably comprises a UV-A sunscreen which is a dibenzoylmethane or its derivatives. Preferred dibenzoylmethane derivatives are selected from 4-tert-butyl-4'-methoxydibenzoylmethane, 2-methyldibenzoylmethane, 4-methyl-dibenzoylmethane, 4-isopropyldibenzoyl-methane, 4-tert-butyldibenzoylmethane, 2,4-dimethyldibenzoylmethane, 2,5-dimethyldibenzoylmethane, 4,4'-diisopropyl-dibenzoylmethane, 2-methyl-5-isopropyl-4'-methoxydibenzoylmethane, 2-methyl-5-tert-butyl-4'-methoxy-dibenzoyl methane, 2,4-dimethyl-4'-methoxy dibenzoylmethane or 2,6-dimethyl-4-tert-butyl-4'-methoxy-dibenzoylmethane. The most preferred dibenzoylmethane derivative is 4-tert.-butyl-4'-methoxydibenzoylmethane. The composition of the invention preferably comprises 0.1 to 10%, more preferably 0.2 to 5%, further more preferably 0.4 to 3%, by weight dibenzoylmethane or a derivative thereof based on total weight of the composition and including all ranges subsumed therein.

The composition may also preferably comprises a UV-B organic sunscreen selected from the class of cinnamic acid, salicylic acid, diphenyl acrylic acid and derivatives thereof. Illustrative non-limiting example of UV-B sunscreens which are commercially available and useful for inclusion in the composition of the invention are Octisalate™, Homosalate™, NeoHelipan™, Octocrylene™, Oxybenzone™ or Parsol MCX™. The UV-B sunscreen is most preferably 2-ethyl-hexyl-4-methoxy cinnamate which is commercially available as Parsol MCX. The UV-B organic sunscreen is preferably included in 0.1 to 10%, more preferably 0.1 to 7% by weight of the composition. It has been observed that presence of an organic UV-B sunscreen like 2-ethyl-hexyl-4-methoxy cinnamate causes further rapid degradation of the UV-A dibenzoylmethane sunscreen in the presence of UV radiation. The presence of the rosmarinic acid ester compound is found to be very efficacious in stabilizing the composition even when UV-B sunscreens are present.

Useful inorganic sun-blocks are also preferably used in the present invention. These include, for example, zinc oxide, iron oxide, silica, such as fumed silica, and titanium dioxide.

Preservatives can also be added into the compositions to protect against the growth of potentially harmful microorganisms. Suitable traditional preservatives for compositions of this invention are alkyl esters of para-hydroxybenzoic acid. Other preservatives which have more recently come into use include hydantoin derivatives, propionate salts, and a variety of quaternary ammonium compounds. Particularly preferred preservatives are phenoxyethanol, methyl paraben, propyl paraben, imidazolidinyl urea, sodium dehydroacetate, benzyl alcohol, alkane diols most preferably 1,2-octane diol and phenoxyethanol. The preservatives should be selected having regard for the use of the composition and possible incompatibility between the preservatives and other ingredients. Preservatives are preferably employed in amounts ranging from 0.01% to 2% by weight of the composition.

A variety of other optional materials may be formulated into the compositions. These may include: antimicrobials such as 2-hydroxy-4,2',4'-trichlorodiphenylether (triclosan), 2,6-dimethyl-4-hydroxychlorobenzene, and 3,4,4'-trichlorocarbanilide; scrub and exfoliating particles such as polyethylene and silica or alumina; cooling agents such as menthol; skin calming agents such as aloe vera; and colorants.

In addition, the compositions may further include 0 to 10% by weight of opacifiers and pearlizers such as ethylene glycol distearate, titanium dioxide or Lytron® 621 (Styrene/Acrylate copolymer); all of which are useful in enhancing the appearance or properties of the product.

Diluents other than water can include liquid or solid emollients, solvents, humectants, thickeners and powders. Examples of each of these types of vehicle, which can be used singly or as mixtures of one or more vehicles, are as follows:

Emollients, such as stearyl alcohol, glyceryl monoricinoleate, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, eicosanyl alcohol, behenyl alcohol, cetyl palmitate, silicone oils such as dimethylpolysiloxane, di-n-butyl sebacate, isopropyl myristate, isopropyl palmitate, isopropyl stearate, butyl stearate, polyethylene glycol, triethylene glycol, lanolin, cocoa butter, corn oil, cotton seed oil, olive oil, palm kernel oil, rape seed oil, safflower seed oil, evening primrose oil, soybean oil, sunflower seed oil, avocado oil, sesame seed oil, coconut oil, arachis oil, castor oil, acetylated lanolin alcohols, petroleum jelly, mineral oil, butyl myristate, isostearic acid, palmitic acid, isopropyl linoleate, lauryl lactate, myristyl lactate, decyl oleate, myristyl myristate;

Solvents, such as ethyl alcohol, isopropanol, acetone, ethylene glycol monoethyl ether, diethylene glycol monobutyl ether, diethylene glycol monoethyl ether;

Advantageously, active agents other than skin conditioning agents defined above may be added to the composition. These active ingredients may be advantageously selected from bactericides, vitamins, anti-acne actives; anti-wrinkle, anti-skin atrophy and skin repair actives; skin barrier repair actives; non-steroidal cosmetic soothing actives; artificial tanning agents and accelerators; skin lightening actives; sunscreen actives; sebum stimulators; sebum inhibitors; anti-oxidants; protease inhibitors; skin tightening agents; anti-itch ingredients; hair growth inhibitors; 5-alpha reductase inhibitors; desquamating enzyme enhancers; antiglycation agents; or mixtures thereof; and the like.

These active agents may be selected from water-soluble active agents, oil soluble active agents, pharmaceutically acceptable salts and mixtures thereof. The term "active agent" as used herein, means personal care actives which can be used to deliver a benefit to the skin and/or hair and which generally are not used to confer a skin conditioning benefit, such are delivered by emollients as defined above. The term "safe and effective amount" as used herein, means an amount of active agent high enough to modify the condition to be treated or to deliver the desired skin care benefit, but low enough to avoid serious side effects. The term "benefit," as used herein, means the therapeutic, prophylactic, and/or chronic benefits associated with treating a particular condition with one or more of the active agents described herein. What is a safe and effective amount of the active agent(s) will vary with the specific active agent, the ability of the active to penetrate through the skin, the age, health condition, and skin condition of the user, and other like factors.

Powders, such as chalk, talc, fullers earth, kaolin, starch, gums, colloidal silica sodium polyacrylate, tetra alkyl and/or trialkyl aryl ammonium smectites, chemically modified magnesium aluminium silicate, organically modified montmorillonite clay, hydrated aluminium silicate, fumed silica, carboxyvinyl polymer, sodium carboxymethyl cellulose, ethylene glycol monostearate.

The cosmetically acceptable base is usually from 10 to 99.9%, preferably from 50 to 99% by weight of the composition, and can, in the absence of other personal care adjuncts, form the balance of the composition.

The composition of the invention may preferably comprises a conventional deodorant base as the cosmetically acceptable carrier. By a deodorant is meant a product in the stick, roll-on, or propellant medium which is used for personal deodorant benefit e.g. application in the under-arm area which may or may not contain anti-perspirant actives.

Deodorant compositions can generally be in the form of firm solids, soft solids, gels, creams, and liquids and are dispensed using applicators appropriate to the physical characteristics of the composition. Deodorant compositions which are delivered through roll-ons generally comprise a liquid carrier. Such liquid carrier can be hydrophobic or comprise a mixture of both hydrophilic and hydrophobic liquids. They may be in the form of an emulsion or a microemulsion. The liquid carrier or mixture of carriers often constitutes from 30 to 95% by weight of the composition and in many instances from 40 to 80%. Hydrophobic liquid carriers commonly can comprise one or more materials selected within the chemical classes of siloxanes, hydrocarbons, branched aliphatic alcohols, esters and ethers that have a melting point not higher than 25° C. and a boiling point of at least 100° C. Hydrophilic carrier liquids that can be employed in compositions herein commonly comprise water and/or a mono or polyhydric alcohol or water-miscible homologue. Monohydric alcohols often are short chain, by which is meant that they contain up to 6 carbons, and in practice is most often ethanol or sometimes iso-propanol. Polyhydric alcohols commonly comprise ethylene or propylene glycol, or a homologue can be employed such as diethylene glycol. Other than this suitable other vehicle and component used for deodorant composition can be added.

When the composition is in the form of a hand sanitizer composition the cosmetically acceptable base may comprises of alcohol and water. The most preferred alcohols are ethyl alcohol and isopropyl alcohol. Even a mixture of two or more alcohol can preferably be used in the hand sanitizer composition. The amount of alcohol preferably in the range of 50 to 95%, more preferably 60 to 80% and most preferably 65 to 80% by weight of the hand sanitizer composition.

The compositions of the present invention can comprise a wide range of other optional components. The CTFA Personal care Ingredient Handbook, Second Edition, 1992, which is incorporated by reference herein in its entirety, describes a wide variety of non-limiting personal care and pharmaceutical ingredients commonly used in the skin care industry, which are suitable for use in the compositions of the present invention. Examples include: antioxidants, binders, biological additives, buffering agents, colorants, thickeners, polymers, astringents, fragrance, humectants, opacifying agents, conditioners, pH adjusters, natural extracts, essential oils, skin sensates, skin soothing agents, and skin healing agents.

The composition of the present invention may also comprises one or more of the following ingredients e.g. benzethonium chloride (BEC), benzalkonium chloride (BKC), chloroxylenol, zinc pyrithione (ZPT), creatine and creatinine.

Leave-on composition preferably means those composition which is not required to be removed from the human body after the application of the composition e.g. skin cream, body lotion, hand sanitizer, deodorants etc.

Wash-off composition preferably means those composition which is intended/required to be removed from the body by washing with solvent preferably water after the application of the composition e.g. hand wash composition, face wash composition etc.

The present invention also discloses a method of cleaning or disinfecting a surface comprising the steps of applying a composition according to the invention on to said surface in case of a leave-on composition. This method optionally comprises an additional step of at least partially removing the composition from the surface if it is in the form of a wash-off composition. Preferably, the step of at least partially removing the composition is carried out less than 5 minutes after the step of applying the composition on the substrate. Preferably, the method is non-therapeutic.

The present invention also discloses a use of a composition of the present invention as disclosed above for improved antimicrobial benefit. Improved antimicrobial benefit preferably means after application of the composition of the present invention the residual microbes on the surface is significantly less. Therefore the composition of the present invention able to provide prolonged/long-lasting antimicrobial benefits.

The present invention also provides use of a composition comprising Niacinamide and picolinamide for inducing secretion of anti-microbial peptides (AMPs) when applied on an external surface of the human body.

The composition comprising niacinamide and picolinamide for use in the present invention preferably induces secretion of AMPs from keratinocytes. The AMPs thus secreted provides for improving the immunity of the external surface of the human body. The external surface includes skin, scalp or oral cavity.

It has been found by way of the present invention that a combination of niacinamide and picolinamide activates keratinocytes, which are the major cells in the skin epidermis to provide the benefits of the present invention viz. inducing secretion of anti-microbial peptides (AMPs). This causes to boost protection shield against germs. The composition comprising niacinamide and picolinamide therefore provides protection for the body against infections by boosting the body's own defence. In other words, the active primes the body surface for germ protection. The advantage of this is that it provides long-lasting protection e.g. up to 24 hours of protection against germs.

The use of the composition of the present invention may preferably for hand hygiene.

The preferred intended use of the composition of the present invention is non-therapeutic and/or cosmetic.

The present invention also discloses the use of the composition for hand hygiene.

Consequently, the present invention also provides use of a combination of nicotinamide and picolinamide in a composition comprising a cosmetically acceptable base for inducing the secretion of anti-microbial peptides. Preferably, the invention provides such use of a synergistic combination of nicotinamide and picolinamide. Thus, the invention preferably provides use of a combination of nicotinamide and picolinamide in a composition comprising a cosmetically acceptable base for synergistically inducing the secretion of anti-microbial peptides. The preferences with regard to the composition of the present invention apply equally to this use according to the invention.

The present invention now will be demonstrated by way of following non-limiting examples.

EXAMPLES

Preparation of the Composition of the Present Invention:

As an example a hand sanitizer composition was prepared as per Table 1, using the method known in the art:

TABLE 1

| Ingredients | Wt % |
| --- | --- |
| Ethyl Alcohol | 62.000 |
| Isopropyl Alcohol | 3.000 |
| Niacinamide | 2.500 |
| Picolinamide | 2.500 |
| Glycerin | 1.000 |
| Perfume | 0.075 |
| Aminomethyl Propanol | 0.147 |
| Tocopheryl Acetate | 0.050 |
| Tetrasodium EDTA | 0.005 |
| Water | To 100 |

Furthermore, a roll-on deodorant composition was also prepared as per Table 2 using the method known in the art:

TABLE 2

| Ingredients | Wt % |
| --- | --- |
| Niacinamide | 2.50 |
| Picolinamide | 2.50 |
| Sunflower seed oil | 4.00 |
| Glycerin | 4.00 |
| Ethoxylated alcohol C18/E2 | 2.60 |
| Ethoxylated alcohol C18/E20 | 0.60 |
| 2-Phenoxyethanol | 0.40 |
| 3-iodo-2-propynyl butyl carbamate, PEG laurate and PEG dilaurate | 0.07 |
| Water | To 100 |

In-Vitro Experiment with Combination of Niacinamide and Picolinamide as Per the Present Invention for Generation of AMP (Psoriasin):

The experiment was done using the following protocol:

Step 1: Human neonatal primary skin keratinocyte (NHEK) cells was obtained from Lonza®. The experiment was done with the above-mentioned cells with passage between 3 and 4. Then, the cells were seeded (35,000 cells/well) in 24 well plate with keratinocyte growth media (KGM) obtained from Invitrogen®. The plate was then incubated at 37±2° C. in a $CO_2$ incubator for 48 hours.

Step 2: After 48 hours of incubation, cell differentiation was induced by replacing media with fresh KGM supplemented with 2 mM calcium chloride solution. This was then followed by incubation at 37±2° C. in a $CO_2$ incubator for 48 hours.

Step 3: After that, the cells were treated with different concentration of Niacinamide and picolinamide and their combination at various concentration as per following Table 3 with keratinocyte growth media supplemented with 2 mM calcium chloride solution:

TABLE 3

| Example No. | Treatment |
| --- | --- |
| A | Control (without Niacinamide and/or picolinamide) |
| B | 5 mM Niacinamide |
| C | 10 mM Niacinamide |
| D | 5 mM picolinamide |
| E | 10 mM picolinamide |
| 1 | 10 mM Niacinamide + 10 mM picolinamide |
| 2 | 5 mM Niacinamide + 10 mM picolinamide |
| 3 | 10 mM Niacinamide + 5 mM picolinamide |

Step 4: After the above treatment, cells were again incubated at 37±2° C. in a $CO_2$ incubator for 72 hours Step 5: After 72 h of incubation, cell culture supernatant from each well was collected in a sterile tube. The samples were then stored at −80° C. until used for testing psoriasin secretion by standard ELISA technique using psoriasin ELISA kit obtained from Circulx® (No: CY—8073). In the current experiment, psoriasin was used as a marker for AMP.

Step 6: The ELISA method was performed by using 100 μL of cell culture supernatant from each sample. The data is expressed in terms of fold change over control (without Niacinamide and/or picolinamide, Example A).

The results are summarized below in Table 4:

TABLE 4

| Example No. | Fold change in psoriasin secretion | SD |
| --- | --- | --- |
| A | 1 | 0 |
| B | 1.8 | 0.26 |
| C | 3.3 | 0.17 |
| D | 3.5 | 0.03 |
| E | 3.8 | 0.68 |
| 1 | 12.8 | 0.81 |
| 2 | 9.4 | 0.93 |
| 3 | 12.1 | 1.22 |

From the above table it is evident that the compositions that are within the scope of the present invention (Examples 1 to 3) provides much better fold change in psoriasin (AMP) secretion than the control examples (Examples B to E). It is also noted that Example B (5 mM niacinamide) and Example E (10 mM picolinamide) when combined together (Example 2) provides synergistic benefit in AMP generation. The synergistic effect is also observed for Example 1 (combination of Example C and Example E) and Example 3 (combination of Example C and Example D).

Therefore, from the above description it is clear that by way of present invention, it is now possible to provide a composition for improved antimicrobial benefit by enhancement in the generation of AMP.

The invention claimed is:

1. A topical composition comprising niacinamide and picolinamide to provide an antimicrobial benefit when applied to an external surface of the human body.

2. The composition as claimed in claim 1, wherein the composition comprises 0.1 to 20% by weight of niacinamide.

3. The composition as claimed in claim 1, wherein the composition comprises 1 to 5% by weight of niacinamide.

4. The composition as claimed in claim 1, wherein the composition comprises 1 to 3% by weight of niacinamide.

5. The composition as claimed in claim 1, wherein the composition comprises 0.1 to 20% by weight of picolinamide.

6. The composition as claimed in claim 1, wherein the composition comprises 1 to 5% by weight of picolinamide.

7. The composition as claimed in claim 1, wherein the composition comprises 1 to 3% by weight of picolinamide.

8. The composition as claimed in claim 1, wherein the molar ratio of niacinamide to picolinamide is from 1:20 to 20:1.

9. The composition as claimed in claim 1, wherein the molar ratio of niacinamide to picolinamide is from 1:15 to 15:1.

10. The composition as claimed in claim 1, wherein the molar ratio of niacinamide to picolinamide is from 1:10 to 10:1.

11. The composition as claimed in claim 1, wherein the molar ratio of niacinamide to picolinamide is from 1:2 to 2:1.

12. The composition according to claim 1, further comprising a cosmetically accepted base.

13. The composition according to claim 1, comprising a skin benefit agent.

14. The composition according to claim 13, wherein the skin benefit agent comprises a skin-lightening agent.

15. The composition according to claim 14, wherein the skin lightening agent comprises 2,4 resorcinol derivatives, 3,5 resorcinol derivatives, green tea extract, vitamins or mixtures thereof.

16. A topical composition comprising picolinamide and green tea extract to provide a skin-lightening benefit.

17. A method for inducing secretion of anti-microbial peptides (AMPs) when applied on an external surface of the human body using the composition of claim 1.

18. The method as claimed in claim 15, wherein the method induces secretion of anti-microbial peptides (AMPs) from keratinocytes.

* * * * *